United States Patent [19]

Byers et al.

[11] Patent Number: 4,801,551
[45] Date of Patent: Jan. 31, 1989

[54] RUGGED DISSOLVED CARBON DIOXIDE MONITOR FOR HIGH PURITY WATER

[75] Inventors: William A. Byers, Penn Hills Township, Allegheny County; Gerald L. Carlson, Mt. Lebanon Twp., Allegheny County, both of Pa.; James C. Bellows, Maitland, Fla.

[73] Assignee: Westinghouse Electric Corp., Pittsburgh, Pa.

[21] Appl. No.: 915,605

[22] Filed: Oct. 6, 1986

[51] Int. Cl.⁴ .................... G01N 33/18; G01N 33/48
[52] U.S. Cl. ...................................... 436/133; 436/68; 436/150
[58] Field of Search .................... 436/133, 150, 68

[56] References Cited

U.S. PATENT DOCUMENTS

| | | |
|---|---|---|
| 2,832,673 | 6/1973 | Larson et al. . |
| 2,901,327 | 3/1972 | Thayer et al. . |
| 2,950,176 | 1/1976 | Thayer et al. . |
| 3,042,495 | 9/1965 | Wilson et al. . |
| 3,158,444 | 4/1974 | Larson et al. . |
| 3,399,037 | 10/1973 | Eckfeldt . |
| 3,531,252 | 2/1975 | Rivers . |
| 3,904,365 | 3/1965 | Larson et al. . |
| 4,003,705 | 1/1977 | Buzza et al. ........................ 436/68 |
| 4,251,219 | 2/1979 | Larson et al. . |
| 4,251,220 | 2/1980 | Larson et al. . |
| 4,272,246 | 6/1981 | Fritz et al. ........................ 436/110 |
| 4,472,354 | 9/1984 | Passell et al. ........................ 422/70 |

*Primary Examiner*—Michael S. Marcus
*Assistant Examiner*—Timothy M. McMahon

[57] ABSTRACT

A continuous on-line monitor of carbon dioxide dissolved in high purity water includes a cation conductivity cell and associated bridge for measuring first and second cation conductivities at first and second temperature and a heater for heating the sample from the first to the second temperature. A microcomputer calculates first and second concentrations of a fully dissociated acid alone and carbon dioxide alone, respectively, which will produce the first measured cation conductivity at the first temperature and then determines the actual carbon dioxide concentration from the first and second concentrations and the second measured cation conductivity.

10 Claims, 9 Drawing Sheets

RUGGED DISSOLVED CARBON DIOXIDE MONITOR FOR HIGH PURITY WATER

BACKGROUND OF THE INVENTION

1. Field of the Invention

The present invention relates to a monitor for determining concentration of dissolved carbon dioxide ($CO_2$) in a fluid sample stream, and more particularly, to a rugged device for continuous online monitoring of dissolved $CO_2$ impurities in steam cycle water used for electrical power generation with both nuclear and fossil fuel steam generation systems.

2. Description of the Related Art

Dissolved carbon dioxide has been recognized as a potent cracking agent in basic solutions and a promoter of general corrosion in acidic solutions for many decades. However, no known on-line monitor exists which provides both high sensitivity and long term reliability. For example, U.S. Pat. No. 4,003,705 to Buzza et al. is directed to a device capable of detecting $CO_2$ concentration with high selectivity by using a sample in a reaction which releases $CO_2$ that in turn is reacted with an electrolyte. The change in pH of the electrolyte is indicative of the amount of $CO_2$ in the sample. The device taught by Buzza et al. is very complex and not particularly sensitive, making it inappropriate for continuous monitoring of high purity water.

Single column ion chromatography is used for carbon dioxide detection in a device taught by U.S. Pat. No. 4,272,246 to Fritz et al. An anion exchange bed and an eluent of a very low electrical conductance organic salt solution, such as a solution of potassium phthalate, precedes a conductivity cell in the device taught by Fritz et al. This device is capable of detecting trace amounts of $CO_2$ in high purity water; however, the construction and operation of the device taught by Fritz et al. is fairly complex and therefore unsuitable for continuous online monitoring in an industrial environment.

Ion chromatography is also used in a continuous system disclosed in U.S. Pat. No. 4,472,354 to Passell et al. which recommends the use of ion chromatograph exclusion for detection of carbonates. While ion chromotography is quite sensitive and it is possible, as taught by Passell et al., to use ion chromatography in a continuous monitor, it is desirable to have a simpler, more rugged $CO_2$ detector with sufficient sensitivity to detect $CO_2$ in the amounts found in the power generation loops of a pressurized light water nuclear reactor or fossil power plants.

SUMMARY OF THE INVENTION

An object of the present invention is to provide a continuous on-line carbon dioxide monitor which is both sensitive and highly reliable.

Another object of the present invention is to provide a continuous on-line carbon dioxide monitor which does not require that any additional substances be supplied for reaction with a sample.

A further object of the present invention is to provide a continuous on-line carbon dioxide monitor which can be calibrated using distilled water.

The above objects are accomplished by a continuous on-line carbon dioxide monitor including temperature changing means for changing a sample from a first temperature to a second temperature; cation conductivity measurement means for measuring first and second measured cation conductivities of the sample at the first and second temperatures, respectively; and concentration determination means for determining actual concentration of carbon dioxide in dependence upon the first and second measured cation conductivities. In a preferred embodiment, the concentration determination means determines first and second concentrations of a fully dissociated acid alone and carbon dioxide alone, respectively, which will produce the first measured cation conductivity at the first temperature, and then determines the actual carbon dioxide concentrations from the first and second concentrations and the second measured cation conductivity.

These objects together with other objects and advantages which will be subsequently apparent, reside in the details of construction and operation as more fully hereinafter described and claimed, reference being had to the accompanying drawings forming a part hereof, wherein like reference numerals refer to like parts throughout.

DESCRIPTION OF THE PREFERRED EMBODIMENTS

Deviations in the electrical conductivity of water provide a good measure of purity. Pure water has a conductivity of 0.055 $\mu$S/cm. The presence of ionic impurities in water will increase the conductivity by an amount which is roughly proportional to the amount of impurities. Commercially available electrical conductivity measuring equipment has high precision and accuracy so that most ions can be sensed below the one part per billion (ppb) level. For this reason electrical conductivity has been used in the electrical power and microcircuit manufacturing industries, among others, to monitor water purity.

However, a conductivity measurement alone only provides an indication of overall purity, without identifying specific contaminants. Conventionally, some form of physical separation of the ionic compounds is used, as described in the U.S. patents discussed above. All of these known devices are relatively complex and while some provide satisfactory sensitivity and have even been applied to continuous on-line monitoring, a more reliable monitor is highly desirable.

Figure 1:
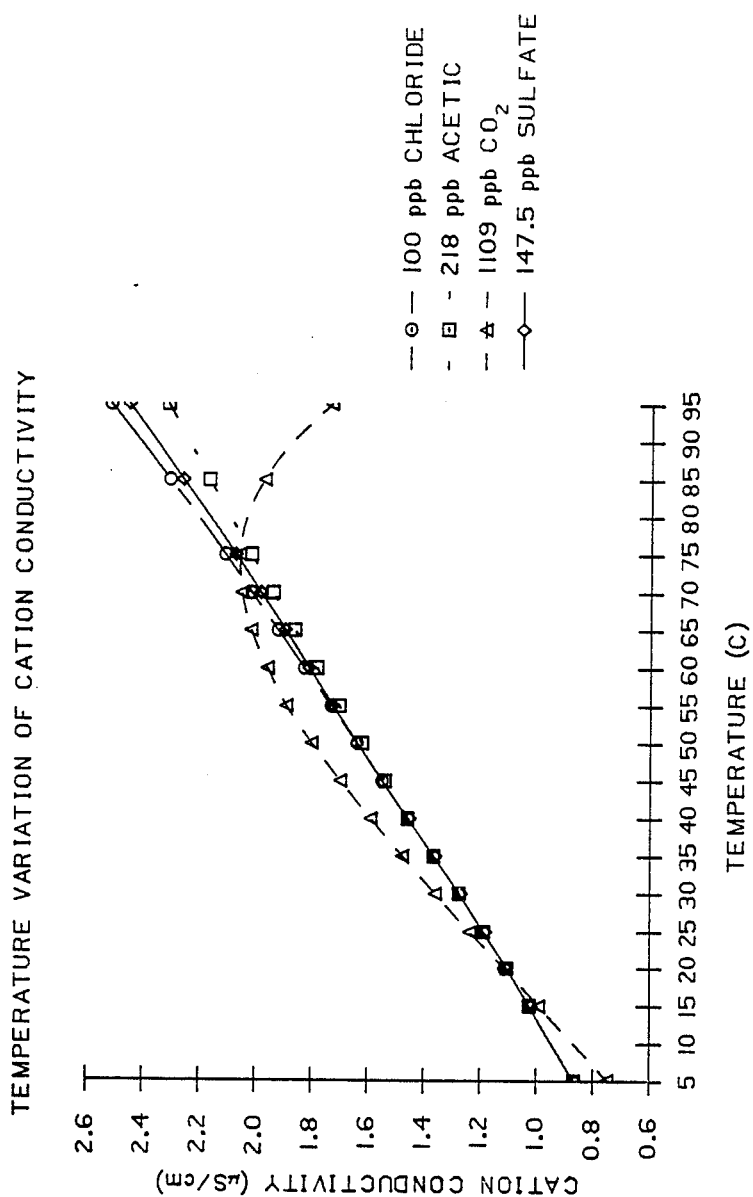
FIG. 1 is a graph of temperature variation of cation conductivity.

According to the present invention, such a device can be constructed to detect carbon dioxide due to differences in the changes of cation conductivity for different substances in response to changes in temperature. As illustrated in FIG. 1, cation conductivity generally increases with an increase in temperature. Solutions of chloride, acetate and sulfate, having identical cation conductivity at 20° C., all respond to increases in temperature in a substantially linear manner. However, a $CO_2$ solution having the same cation conductivity at 20° C. has a significantly different curve which, for the illustrated concentration of 1109 ppb, flattens out at approximately 75° C. and dips downward at higher temperatures. The differences in the behavior of carbonic cation conductivity and the cation conductivity of the other three substances are believed to be due to the fact that chloride, acetate and sulfate solutions are fully dissociated while the following temperature dependent equilibrium equation applies to dissolved $CO_2$.

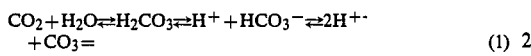
(1)

Carbonic acid has an acid dissociation constant Ka which is defined in equation (2) below.

$$Ka = \frac{[H^+][HCO_3^-]}{[H_2CO_3]} \quad (2)$$

Figure 2:
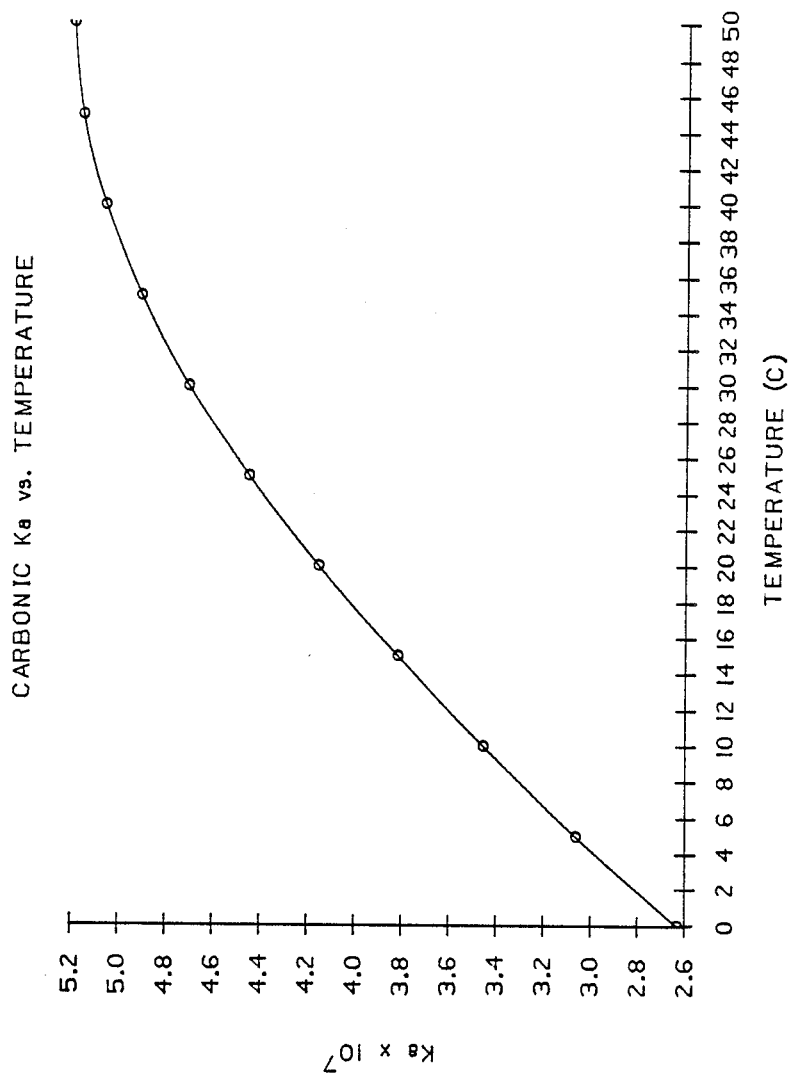
FIG. 2 is a graph of the temperature variation of the acid dissociation constant (Ka) of carbonic acid.

The temperature variation of carbonic Ka is illustrated in FIG. 2 using values from the Chemical Rubber Company Handbook of Chemistry and Physics. Using least squares analysis, the formula in equation (3) has been derived for the curve illustrated in FIG. 2.

$$Ka = -6.2316e^{-6}T^3 - 3.9977e^{-4}T^2 + 0.086518\,T + 2.6292 \quad (3)$$

Figure 3:
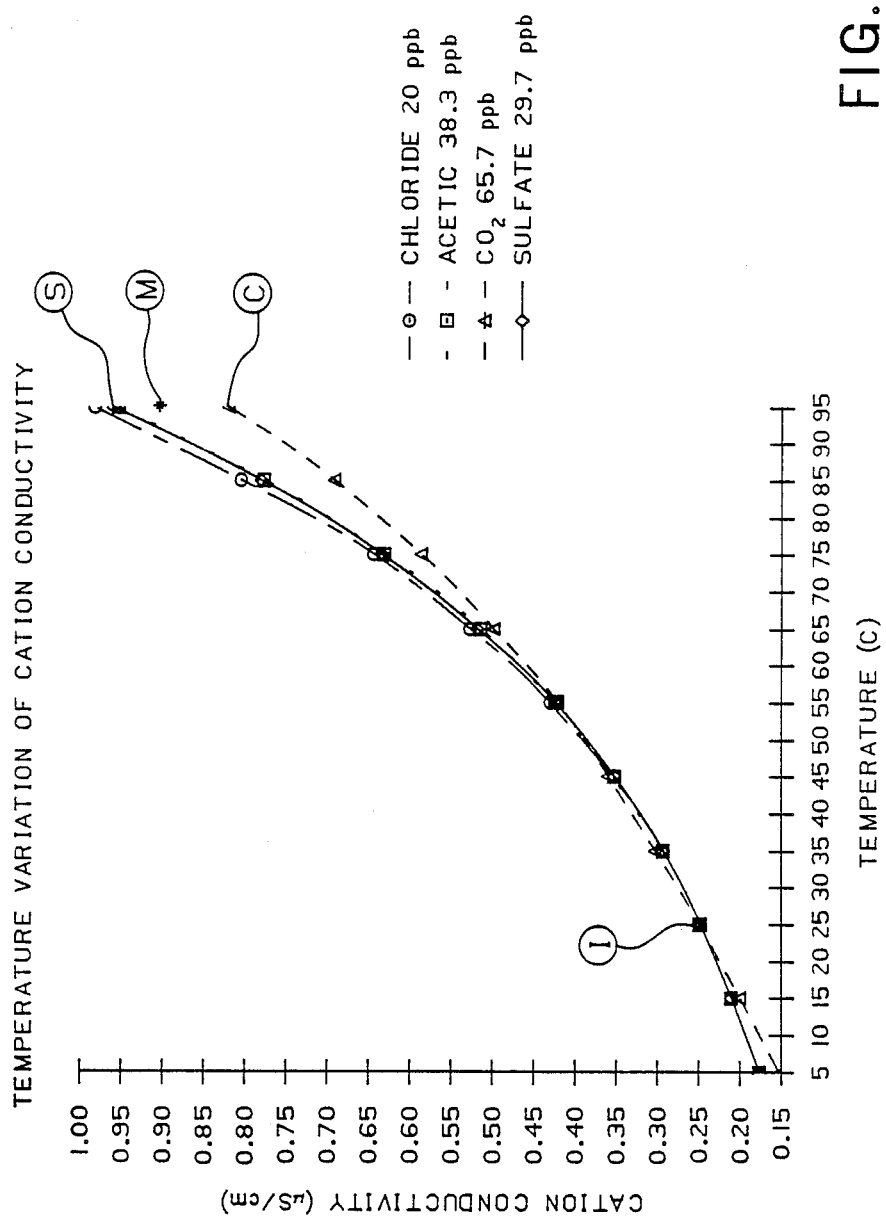
FIG. 3 is a graph of temperature variation of cation conductivity.

The concentrations of the acids used for FIG. 2 are relatively high. However, even when much lower concentrations of acids are used, the deviation of $CO_2$ compared to sulfate, etc., can be seen. FIG. 3 illustrates temperature variation of cation conductivity for chloride, acetate, sulfate, and bicarbonate concentrations all of which have a cation conductivity of 0.249 μS/cm at 25° C. This amount of cation conductivity will be used as an example below. However, it is be understood that the measured cation conductivity at 25° C. will vary over time and will depend upon the age and type of equipment in the system being monitored.

Determination of $CO_2$ concentration is accomplished according to the present invention by measuring cation conductivity at two different temperatures in order to calculate what portion of the cation conductivity is due to the presence of $CO_2$. A water sample from an electrical power generation system will typically contain impurities of several different ionic contaminants. It is assumed that all of the substances contributing to cation conductivity, except for $CO_2$, have virtually identical temperature variation curves. As a result, it can be assumed that the only substances causing cation conductivity in a sample are water, $CO_2$ and a fully dissociated acid such as hydrogen sulfate or hydrogen chloride. Some electrical power generation systems include a significant amount of ammonia or other volatile ionic amines which mask the conductivity contribution of other impurities. In such systems, it is necessary to pass samples through a cation exchange resin to remove the ammonia but allow anionic species to pass through. Cations other than ammonia are replaced by hydrogen ions prior to the analysis described below.

Figure 4:
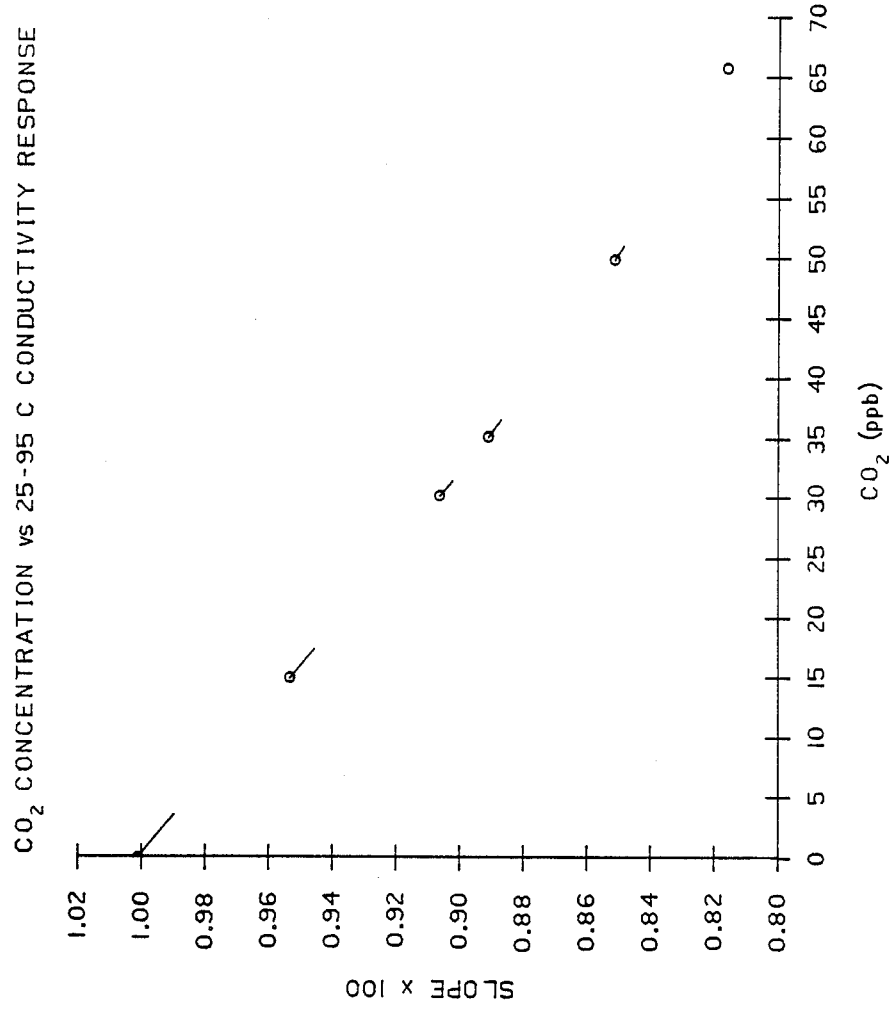
FIG. 4 is a graph of the change in conductivity of solutions having indentical conductivity at 25° C., but varying concentrations of $CO_2$.

The effect of various quantities of $CO_2$ on the change in ion conductivity from 25° C. to 95° C. is illustrated in FIG. 4. Using the cation conductivities plotted in FIG. 3, a solution of sulfate alone in water, which has a cation conductivity of 0.249 μS/cm at 25° C., is expected to have a cation conductivity of 0.952 at 95° C., while a solution of $CO_2$ alone, which has a cation conductivity of 0.249 μS/cm, is predicted to have a cation conductivity of 0.825 μS/cm at 95° C. The concentrations of sulfate and $CO_2$ which have these cation conductivities figures are 29.7 ppb and 65.7 ppb, respectively.

The slope of the line connecting points Ⓘ and Ⓢ in FIG. 3 is $1.00 \times 10^{-2}$ while the slope of the line between points Ⓘ and Ⓒ is $0.821 \times 10^{-2}$, where points Ⓢ and Ⓒ represent solutions of sulfate alone and $CO_2$ alone, respectively, and Ⓘ represents the initial cation conductivity measurement at 25° C. Thus, slope values can be plotted in FIG. 4 where a solution of sulfate alone with 0 ppb $CO_2$ is located along the X-axis and the slope of the line connecting points Ⓘ and Ⓒ for a solution having 65.7 ppb $CO_2$ is represented the point in the lower right hand corner of FIG. 4 indicating a slope of approximately $0.82 \times 10^{-2}$. Four other points are plotted in FIG. 4 for solutions having 15, 30, 35, and 50 ppb $CO_2$ and a sufficient amount of sulfate to provide a cation conductivity of 0.249 μS/cm at 25° C.

Upon inspecting FIG. 4, it can be seen that the change in slope of cation conductivity between 25° an 95° C. in response to increases in $CO_2$ is approximately linear. Thus, if a sample is measured to have a cation conductivity of 0.249 μS/cm at 25° C. and a cation conductivity of 0.90 μS/cm at 95° C. (point Ⓜ in FIG. 3), then the concentration of $CO_2$ can be calculated from the concentration of $CO_2$ alone which will result in the cation conductivity measured at 25° C. by linear interpolation using FIG. 4 or according to equation (4) below.

$$CO_2 \text{ conc} = \left(\frac{S - M}{S - C}\right) CO_2 \text{ alone} \quad (4)$$

For the above example, S (predicted cation conductivity at 95° C. for a solution of sulfate alone which has the measured cation conductivity at 25° C.) is 0.952 μS/cm, M (the measured cation conductivity at 95° C.) is 0.90 μS/cm and C (predicted cation conductivity of a solution of $CO_2$ alone which has the measured cation conductivity at 25° C.) is 0.825 μS/cm. The concentration of $CO_2$ alone is 65.7 ppb, thus producing a result of 26.9 ppb as the actual concentration of $CO_2$. If the four intermediate points plotted in FIG. 4 are taken into consideration and a best fit line is drawn, a value of approximately 23 ppb results for the actual concentration of $CO_2$. If a polynomial approximation method is used for the points in FIG. 4, some other value within 2 ppb of 25 ppb will likely result. Any of these methods may be used in calculating the actual concentration of $CO_2$ to provide a reasonably accurate result.

Figure 5:
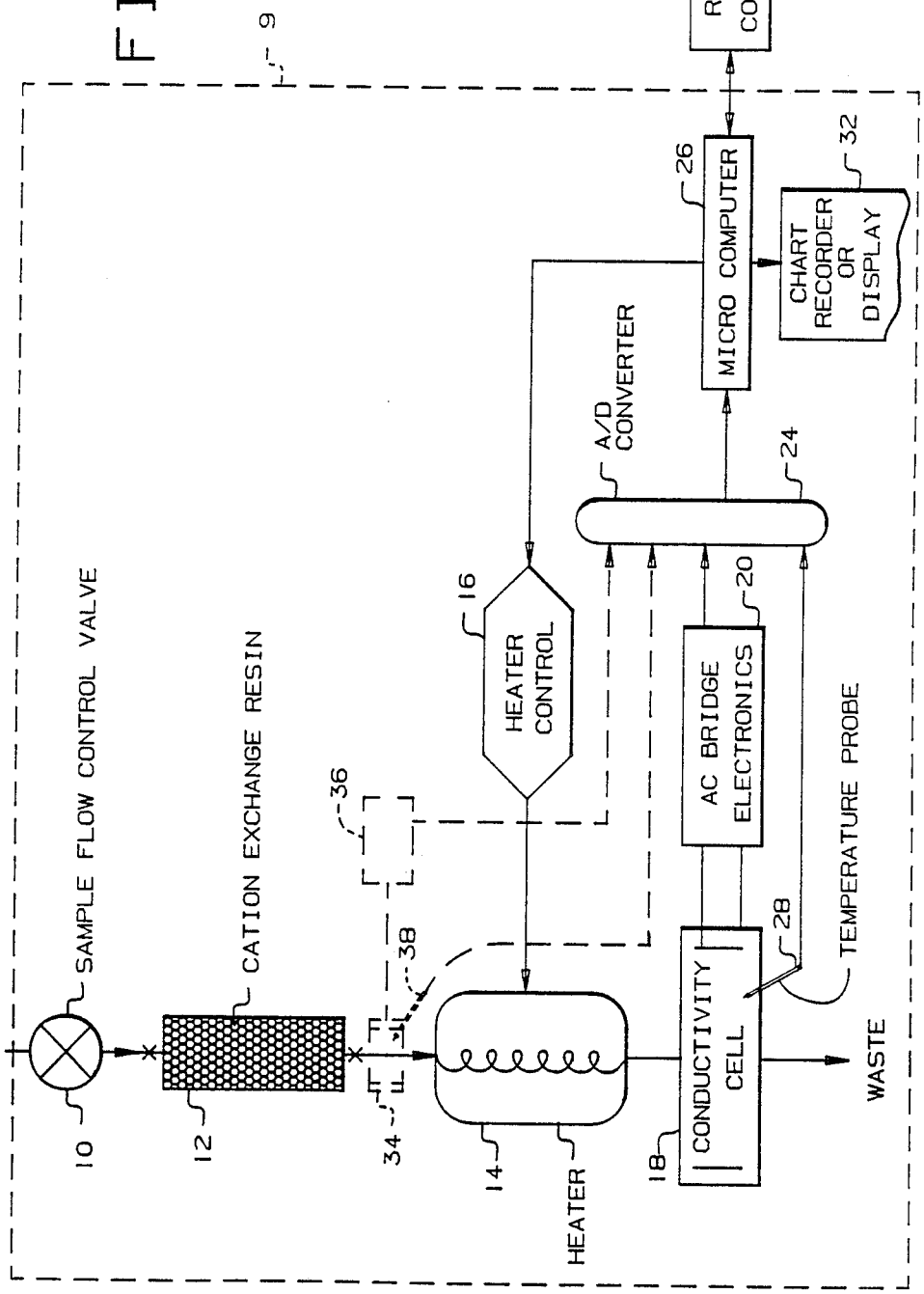
FIG. 5 is a block diagram of a $CO_2$ monitor according to the present invention.

An embodiment of a dissolved $CO_2$ monitor 9 is illustrated in FIG. 5. The problem noted above regarding the masking of cations by the relatively large quantity of ammonia often found in power generation water is avoided by passing a sample selected by sample flow control valve 10, through a cation exchange resin 12, such as an AG 50 manufactured by BIO-RAD of Richmond, Calif., to remove ammonia ions and replace remaining cations with hydrogen ions. After passing through the cation exchange resin 12, the sample is cyclically heated in a heater 14 at a temperature determined by heate control 16. The heater may be, for example, a Fisher Scientific 11-463-115A from Fisher of Pittsburgh, Pa. and the heater control may a model CN 300 JC manufactured by Omega Engineering, Inc. of Stamford, Conn. The conductivity of the sample is measured at the two temperatures in a conductivity cell 18, such as a DIONEX 35220, from Dionex of Sunnyvale, Calif. which includes the necessary AC bridge electronics 20 to provide an analog signal indicating the electrical conductivity of the sample. The analog signal is converted to a digital signal by an analog/digital (A/D) converter 24. A microcomputer 26 receives the digital conductivity signal and is also connected to the heater control 16 for controlling the cycle of the heater 14.

The microcomputer 26 calculates the $CO_2$ concentration by recording the electrical conductivity of the sample at two or more temperatures measured by temperature probe 28 which may be a SICSS-010G-6 from Omega Engineering, Inc. The results of the calculation can be provided to a remote computer 33 as well as a chart recorder or display 32. In most applications, the microcomputer 26 and A/D converter 24, as a combined unit, can be satisfied by several different types of units, one example is an ACTION 5531 computer with an ACTION A1 04 A/D converter available from Action of San Diego, Calif. A MOLYTEK 2702 chart recorder from Molytek of Pittsburgh, Pa. or another display device 32 or remote computer 33 could be connected to receive the results of the monitoring.

In an alternative embodiment, a second conductivity cell 34 and AC bridge 36 with an associated temperature probe 38 could be used to detect conductivity at the first temperature while the first combination could be used for the second and higher temperature. In this embodiment, the heater 14 would be controlled to maintain a constant output temperature.

Figure 6:
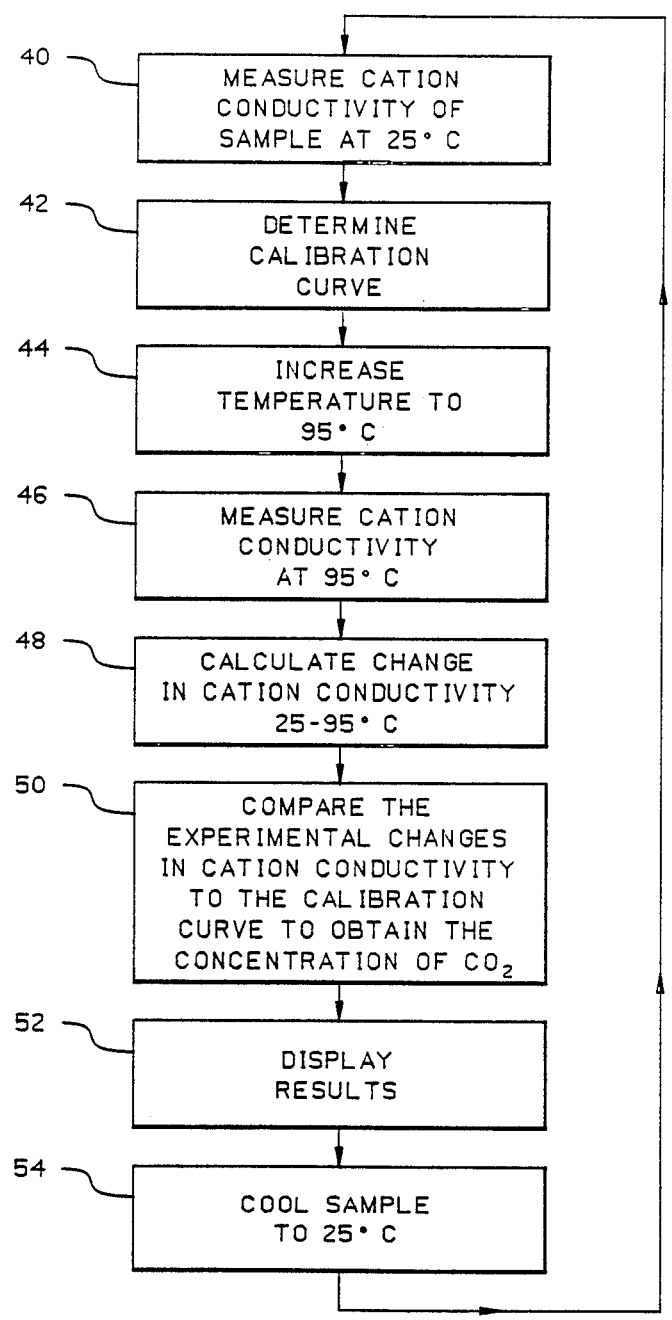
FIG. 6 is a flow chart of a method for continuous determination of $CO_2$ concentration according to the present invention.

The microcomputer 26 could be used for other data gathering or process control applications, but would include a program which would perform the steps illustrated in the flowchart of FIG. 6. As noted above, the cation conductivity will vary over time, therefore the first step of the program is to measure 40 cation conductivity at a first temperature, e.g., 25° C. and then calculate 42 a calibration curve for that cation conductivity. After the temperature of the sample is increased 44 to a second temperature, e.g., 95° C., a second measurement 46 of cation conductivity is made and the change in measured cation conductivity between these two temperatures is calculated 48. The result of these calculations is used to determine 50 the concentration of $CO_2$ and the results are displayed 52. If a single conductivity cell 18 is used, the heater must be cooled down 54 prior to repeating the procedure.

Figure 7:
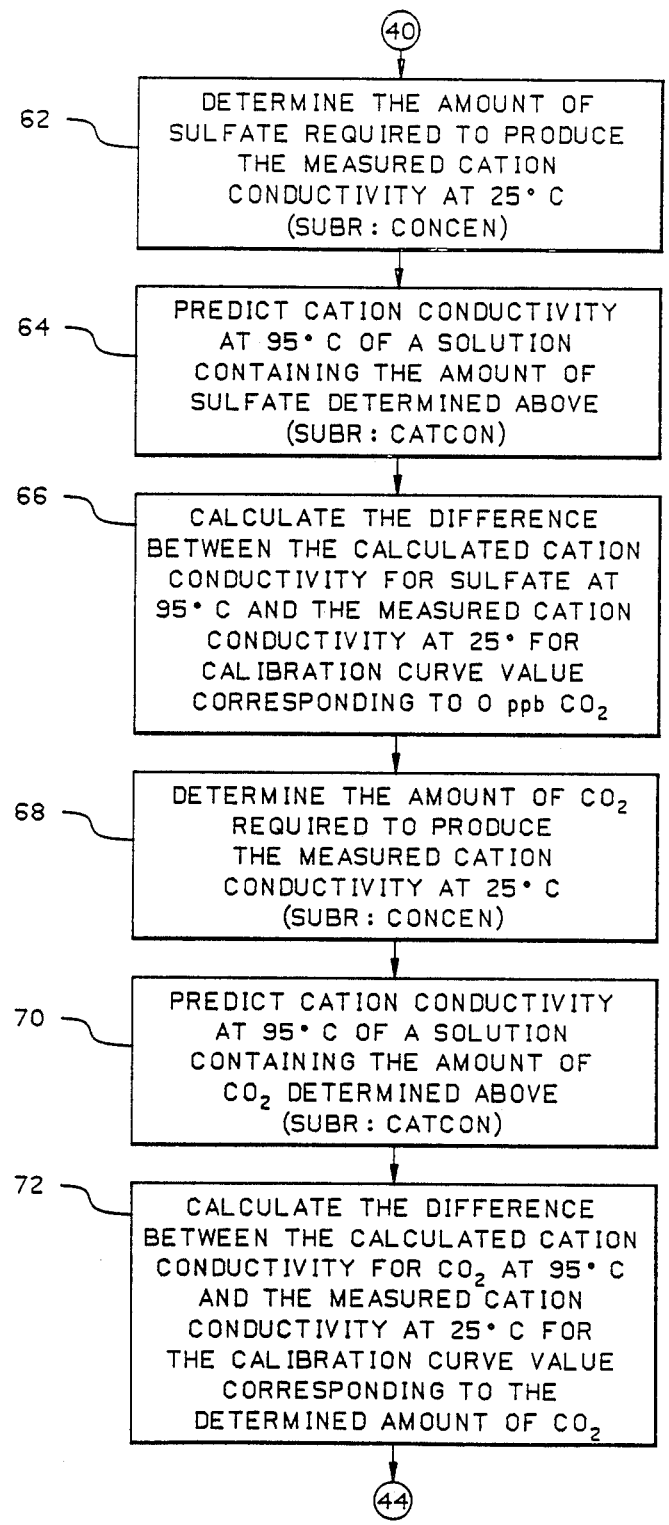
FIG. 7 is a flow chart of the calibration calculations performed in block 42 of FIG. 6.

Calculation of the calibration curve is illustrated in the flowchart in FIG. 7. First, it is necessary to calculate 62 the amount of sulfate (or another fully dissociated acid) required to provide the measured cation conductivity at 25° C. Using this figure, a predicted cation conductivity at 95° for a solution containing the same amount of sulfate alone can be determined 64. The difference between the measured cation conductivity at 25° C. and predicted cation conductivity of sulfate alone at 95° C. provides 66 a calibration curve value corresponding to zero ppb $CO_2$. These three steps are repeated for a solution of $CO_2$ in steps 68, 70 and 72.

Figure 8:
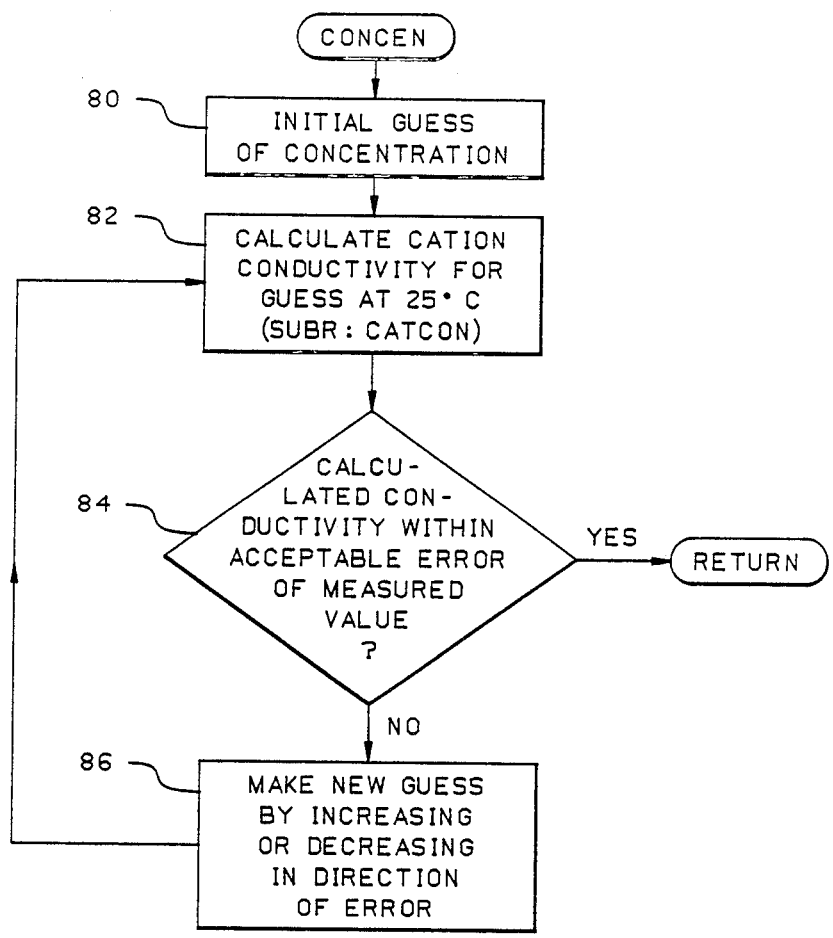
FIG. 8 is a flow chart of subroutine CONCEN called by blocks 62 and 68 in FIG. 7.

More than one method can be used for determining the amount of sulfate alone and $CO_2$ alone required to provide the measured cation conductivity at 25° C. A table of values for sulfate and $CO_2$ containing the concentrations which provide specific cation conductivities at 25° C. and a table look-up could be performed in steps 62 and 68. Alternatively, subroutine CONCEN, illustrated in FIG. 8, can be used to determine the concentration of sulfate and $CO_2$ by successive approximation. Separate subroutines could be used for each substance or a single subroutine could be used with an input argument indicating which of the substances is to have its concentration determined. The initial approximation 80 of concentrtion will be some expected value for the first sample, but thereafter, the previous calculated concentration can be used to minimize the number of iterations of step 82 before step 84 determines that the calculated conductivity is within an acceptable error of the measured value. A new approximation 86 can be made by slowly incrementing or decrementing the previous approximation or estimating the needed change as the difference between calculated and measured values.

Figure 9:
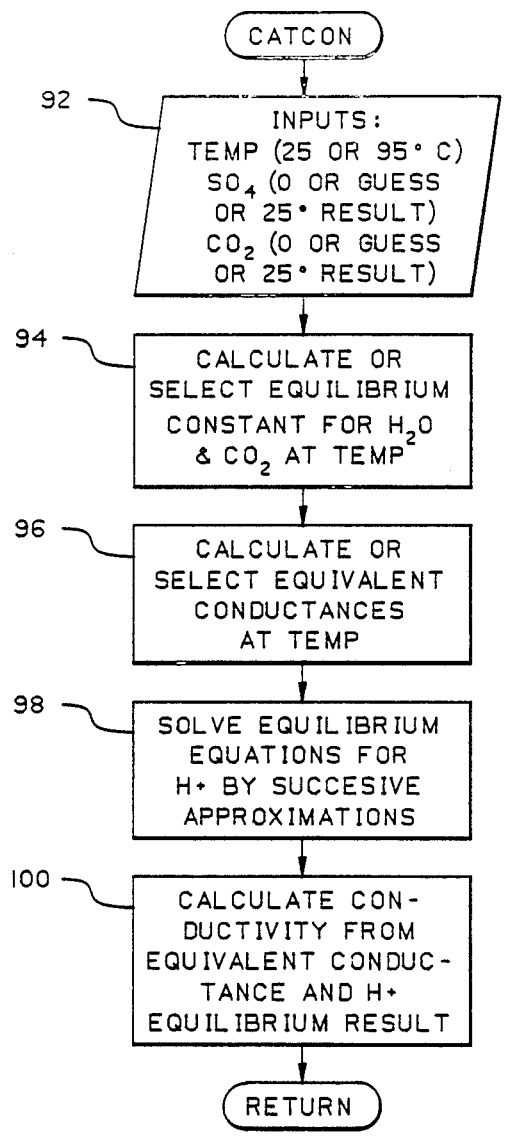
FIG. 9 is a flow chart of subroutine CATCON called by blocks 64 and 70 in FIG. 7.

The predicted cation conductivity calculated in blocks 64 for sulfate and 70 for $CO_2$ could also be determined by a table look-up. Alternatively, subroutine CATCON, illustrated in FIG. 9, can be used. If the CATCON subroutine is used for calculating conductivity of an approximation in step 82 of FIG. 8, the inputs 92 will include temperature as well as the sulfate and $CO_2$ concentration. Since the equilibrium equations for water and carbon dioxide are temperature dependent, the acid dissociation constant Ka for each must be calculated 94 or selected prior to calculating equivalent conductances and solving 98 the equilibrium equations for $H^+$ by e.g., successive approximation. The conductivity can then be calculated 100 from the equivalent conductance and the $H^+$ equilibrium result.

Other methods may possibly be used as alternatives to the table look-ups and the iterative or successive approximation methods described above. For example, it may be possible to develop equations like equation (3) from empirical studies to relate electrical conductivity to concentration of sulfate alone, of $CO_2$ alone, or such concentrations to predicted cation conductivity at e.g., 95° C. Also, the sample could be selected at a high temperature point and measured a second time after cooling.

The many features and advantages of the present invention are apparent from the detailed specification and thus it is intended by the appended claims to cover all such features and advantages of the dissolved carbon dioxide monitor which fall within the true spirit and scope of the invention. Further, since numerous modifications and changes will readily occur to those skilled in the art, it is not desired to limit the invention to the exact construction and operation illustrated and described, accordingly, all suitable modifications and equivalents may be resorted to, falling within the scope of the invention.

What is claimed is:

1. A method of determining dissolved carbon dioxide concentration in a sample, comprising the steps of:
    (a) measuring a first cation conductivity in the sample at a first temperature;

(b) measuring a second cation conductivity in the sample at a second temperature different from the first temperature; and (c) determining an actual concentration of carbon dioxide in the sample in dependence upon the first and second measured cation conductivities.

2. A method as recited in claim 1, wherein step (c) comprises the steps of:
(ci) determining a first concentration of a fully dissociated acid which will produce the first measured cation conductivity at the first temperature;
(cii) determining a second concentration of carbon dioxide which will produce the first measured cation conductivity at the first temperature; and
(ciii) determining the actual concentration of carbon dioxide in dependence upon the first and second concentrations and the second measured cation conductivity.

3. A method as recited in claim 2, wherein the fully dissociated acid is one of hydrogen sulfate and hydrogen chloride.

4. A method as recited in claim 2,
wherein step (ciii) comprises the steps of:
(ciii1) determining a first predicted cation conductivity of the first concentration of tne fully dissociated acid alone at the second temperature;
(ciii2) determining a second predicted cation conductivity of the second concentration of carbon dioxide alone at the second temperature;
(ciii3) calculating a first difference between the first predicted and second measured cation conductivities;
(ciii4) calculating a second difference between the first and second predicted cation conductivities;
(ciii5) calculating a ratio factor by dividing the first difference by the second difference; and
(ciii6) calculating the actual concentration of carbon dioxide by multiplying the second concentration of carbon dioxide by the ratio factor.

5. A method as recited in claim 4, wherein the fully dissociated acid is one of hydrogen sulfate and hydrogen chloride.

6. A method as recited in claim 2,
wherein step (ciii) comprises the steps of:
(ciii1) determining a first predicted cation conductivity of the first concentration of the fully dissociated acid at the second temperature;
(ciii2) determining a second predicted cation conductivity of the second concentration of carbon dioxide alone at the second temperature;
(ciii3) determining a first slope of a first line connecting first and second points representing the first measured and first predicted cation conductivities, respectively, plotted versus temperature;
(ciii4) determining a second slope of a second line connecting the first point and a third point representing the second predicted cation conductivity, plotted versus temperature;
(ciii5) determining a third slope of a third line connecting the first point and a fourth point representing the second measured cation conductivity, plotted versus temperature; and
(ciii6) determining the actual concentration of carbon dioxide from the first, second and third slopes.

7. A method as recited in claim 6, wherein the fully dissociated acid is one of hydrogen sulfate and hydrogen chloride.

8. A method as recited in claim 6,
wherein step (ciii6) comprises the steps of:
(ciii6A) determining a fourth slope of a fourth line connecting fourth and fifth points representing the first and second slopes, respectively, plotted versus carbon dioxide concentration, where the fourth point has zero carbon dioxide concentration; and
(ciii6B) determining the actual concentration of carbon dioxide which corresponds to an X-coordinate of a sixth point on the fourth line, the third slope corresponding to a Y-coordinate of the sixth point.

9. A method as recited in claim 8, wherein the fully dissociated acid is one of hydrogen sulfate and hydrogen chloride.

10. A methodf for determining carbon dioxide concentration in a sample of water used for electrical power generation, comprising the steps of:
(a) measuring a first cation conductivity of the sample at a first temperature;
(b) determining a first concentration of sulfate which alone will produce the first measured cation conductivity at the first temperature;
(c) determining a second concentration of carbon dioxide which alone will produce the first measured cation conductivity at the first temperature;
(d) heating the sample to a second temperature different from the first temperature;
(e) measuring a second cation conductivity of the sample at the second temperature;
(f) determining first and second predicted cation conductivities of the first and second concentrations of sulfate alone and carbon dioxide alone, respectively, at the second temperature; and
(g) determining the actual carbon dioxide concentration in dependence upon the second concentration of carbon dioxide and differences between the second measured and first and second predicted cation conductivities.

* * * * *